United States Patent
Wang et al.

(10) Patent No.: US 7,361,788 B2
(45) Date of Patent: Apr. 22, 2008

(54) DIRECT ALKYLATION OF N-ALKYL-N'-PHENYL-P-PHENYLENEDIAMINE

(75) Inventors: Jin-Yun Wang, Cheshire, CT (US); Huiling Ding, Cheshire, CT (US); Joseph F. Stieber, Prospect, CT (US)

(73) Assignee: Chemtura Corporation, Middlebury, CT (US)

( * ) Notice: Subject to any disclaimer, the term of this patent is extended or adjusted under 35 U.S.C. 154(b) by 0 days.

(21) Appl. No.: 11/339,231

(22) Filed: Jan. 24, 2006

(65) Prior Publication Data

US 2007/0173668 A1    Jul. 26, 2007

(51) Int. Cl.
    *C07C 211/00* (2006.01)
(52) U.S. Cl. .................................... 564/305
(58) Field of Classification Search ............... 564/305
    See application file for complete search history.

(56) References Cited

U.S. PATENT DOCUMENTS

| | | | | |
|---|---|---|---|---|
| 2,762,845 A | * | 9/1956 | Ebersberger et al. | 564/409 |
| 2,814,646 A | | 11/1957 | Kolka et al. | 260/577 |
| 3,275,690 A | | 9/1966 | Stroh et al. | 260/576 |
| 3,649,693 A | | 3/1972 | Napolitano | 260/578 |
| 3,654,331 A | * | 4/1972 | Klopfer et al. | 556/176 |
| 3,923,892 A | * | 12/1975 | Klopfer | 564/409 |
| 5,371,289 A | | 12/1994 | Cottman et al. | 564/396 |

* cited by examiner

*Primary Examiner*—Yvonne Eyler
*Assistant Examiner*—Kellette Gale
(74) *Attorney, Agent, or Firm*—James Sher

(57) ABSTRACT

A single-step process is disclosed for the ring alkylation of at least one N-alkyl-N'-phenyl-phenylenediamine with at least one olefin wherein the process comprises heating a mixture of the N-alkyl-N'-phenyl-phenylenediamine(s) and olefin(s) in the presence of a catalytic amount of at least one alkyl aluminum halide at a temperature of from about 50 to about 350° C. in a sealed vessel for from about one to about 30 hours.

13 Claims, No Drawings

DIRECT ALKYLATION OF N-ALKYL-N'-PHENYL-P-PHENYLENEDIAMINE

BACKGROUND OF THE INVENTION

1. Field of the Invention

The present invention relates to alkylated N-alkyl-N'-phenyl-p-phenylenediamines. More particularly, the present invention relates to a method for the ring alkylation of N-alkyl-N'-phenyl-p-phenylenediamines.

2. Description of Related Art

Aromatic amines are useful in a broad range of applications. For example, they are antiknock agents in gasoline used in spark ignited internal combustion engines. They are also valuable intermediates in the dye industry and are beneficial when added to rubber, where they prevent degradation caused by ozone.

N-substituted-N'-p-phenylenediamines are also known to be useful in the production of drugs, agricultural products, and as dyes, antioxidants, antiozonants, gel inhibitors, and polymerization inhibitors for rubber.

Methods of orthoalkylating aromatic amines, such as aniline, are known. Suitable methods are disclosed in U.S. Pat. No. 2,762,845; U.S. Pat. No. 2,814,646; and U.S. Pat. No. 3,275,690.

U.S. Pat. No. 2,762,845 discloses a procedure for production of alkylated aromatic amines by reaction of aromatic amines and olefins, the procedure being characterized in that aluminum or aluminum alloys can be used to catalyze the alkylation reaction.

U.S. Pat. No. 2,814,646 discloses reacting aromatic amines, having at least one hydrogen on the amino nitrogen and also having at least one hydrogen on a nuclear carbon atom ortho to the amino nitrogen group, with an organic compound possessing one or more units of carbon-to-carbon unsaturation in the presence of an aluminum anilide-type catalyst.

U.S. Pat. No. 3,275,690 discloses the nuclear alkylation of an aromatic amine by reacting an olefin of the group aliphatic olefins and cycloolefins with a aromatic amine at a temperature of about 150-400° C. in the presence of a Friedel-Crafts catalyst.

U.S. Pat. No. 3,649,693 discloses the selective ortho-alkylation of aromatic amines such as aniline with an olefin in the presence of an aluminum anilide catalyst. The orthoalkylated product is distilled from the reaction mixture without prior hydrolysis and the residue remaining can be recycled as the catalyst for a subsequent orthoalkylation process.

U.S. Pat. Nos. 3,654,331 and 3,923,892 disclose the selective ortho-alkylation of aromatic amines having a hydrogen atom on at least one nuclear carbon atom ortho to an amine group (e.g., aniline) by adding a catalytic amount of an alkyl aluminum halide, such as diethyl aluminum chloride to the aromatic amine and then heating the resultant mixture to about 100-500° C. in the presence of an olefin. The process may also be carried out in the added presence of an aluminum anilide.

U.S. Pat. No. 5,371,289 discloses a process for the preparation of a N-substituted-N'-phenyl-p-phenylenediamine comprising reacting (a) a mixture of (1) N-phenyl-p-quinoneimine and (2) p-hydroxydiphenylamine in a mole ratio of N-phenyl-p-quinoneimine to p-hydroxydiphenylamine of from 1.5:1 to 1:1.5 with (b) a primary amine in the presence of methanol.

The disclosures of the foregoing are incorporated herein by reference in their entirety.

SUMMARY OF THE INVENTION

The present invention is directed to the single step ring alkylation of N-alkyl-N'-phenyl-phenylenediamines by heating a mixture of an N-alkyl-N'-phenyl-phenylenediamine and one or more olefins, preferably under pressure, in the presence of a catalytic amount of an alkyl aluminum halide.

More particularly, the present invention is directed to a single-step process for the ring alkylation of at least one N-alkyl-N'-phenyl-phenylenediamine with at least one olefin comprising heating a mixture of the N-alkyl-N'-phenyl-phenylenediamine(s) and olefin(s) in the presence of a catalytic amount of at least one alkyl aluminum halide at a temperature of from about 50 to about 350° C. in a sealed vessel for from about one to about 30 hours.

DESCRIPTION OF THE PREFERRED EMBODIMENTS

As noted above, the present invention is directed to a single-step process for the ring alkylation of at least one N-alkyl-N'-phenyl-phenylenediamine with at least one olefin comprising heating a mixture of the N-alkyl-N'-phenyl-phenylenediamine(s) and olefin(s) in the presence of a catalytic amount of at least one alkyl aluminum halide at a temperature of from about 50 to about 350° C. in a sealed vessel for from about one to about 30 hours.

In a preferred embodiment of the present invention, the N-alkyl-N'-phenyl-phenylenediamine is of the structure:

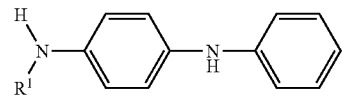

wherein $R^1$ is selected from the group consisting of alkyl, cycloalkyl, and radicals of the structural formula:

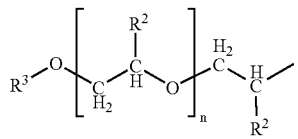

wherein $R^2$ may be the same or different and is independently selected from the group consisting of hydrogen and methyl, $R^3$ is selected from the group consisting of alkyl of from 1 to 12 carbon atoms and n is an integer of from 0 to 6.

With respect to the above phenylenediamine formula, preferably $R^1$ is selected from the group consisting of alkyls having from 1 to 50 carbon atoms and cycloalkyls having from 3 to 30 carbon atoms.

A method for preparing the N-alkyl-N'-phenyl-phenylenediamines employed in the practice of the present invention is described in U.S. Pat. No. 5,371,289, the disclosure of which is incorporated herein by reference. These N-alkyl-N'-phenyl-phenylenediamines can also be prepared by other means known to those skilled in the art.

The N-alkyl-N'-phenyl-phenylenediamines that can be employed in the practice of the present invention include, but are not limited to, the following:
N-methyl-N'-phenyl-p-phenylenediamine,
N-ethyl-N'-phenyl-p-phenylenediamine,
N-propyl-N'-phenyl-p-phenylenediamine, N-isopropyl-N'-phenyl-p-phenylenediamine,
N-n-butyl-N'-phenyl-p-phenylenediamine,
N-sec-butyl-N'-phenyl-p-phenylenediamine,
N-n-pentyl-N'-phenyl-p-phenylenediamine,
N-1-methylbutyl-N'-phenyl-p-phenylenediamine,
N-(1-methylheptyl)-N'-phenyl-p-phenylenediamine,
N-1,2-dimethylpropyl-N'-phenyl-p-phenylenediamine,
N-2-methylbutyl-N'-phenyl-p-phenylenediamine,
N-3-methylbutyl-N'-phenyl-p-phenylenediamine,
N-1-ethylpropyl-N'-phenyl-p-phenylenediamine,
N-n-hexyl-N'-phenyl-p-phenylenediamine,
N-1-methylpentyl-N'-phenyl-p-phenylenediamine,
N-2-methylpentyl-N'-phenyl-p-phenylenediamine,
N-3-methylpentyl-N'-phenyl-p-phenylenediamine,
N-4-methylpentyl-N'-phenyl-p-phenylenediamine,
N-1,2-dimethylbutyl-N'-phenyl-p-phenylenediamine,
N-1,3-dimethylbutyl-N'-phenyl-p-phenylenediamine,
N-1-ethylbutyl-N'-phenyl-p-phenylenediamine,
N-2-ethylbutyl-N'-phenyl-p-phenylenediamine,
N-heptyl-N'-phenyl-p-phenylenediamine,
N-octyl-N'-phenyl-p-phenylenediamine,
N-nonyl-N'-phenyl-p-phenylenediamine, N-decyl-N'-phenyl-p-phenylenediamine,
N-cyclooctyl-N'-phenyl-p-phenylenediamine,
N-cyclohexyl-N'-phenyl-p-phenylenediamine,
N-methylcyclohexyl-N'-phenyl-p-phenylenediamine, and
N-cyclooctyl-N'-phenyl-p-phenylenediamine.

Preferably, the N-alkyl-N'-phenyl-phenylenediamine is selected from the group consisting of:
N-(1,3-dimethylbutyl)-N'-phenyl-p-phenylenediamine,
N-isopropyl-N'-phenyl-p-phenylenediamine,
N-(1-methylheptyl)-N'-phenyl-p-phenylenediamine, and
N-cyclohexyl-N'-phenyl-p-phenylenediamine.

N-(1,3-dimethylbutyl)-N'-phenyl-p-phenylenediamine and N-isopropyl-N'-phenyl-p-phenylenediamine, which are commercially available as Flexzone 7 and Flexzone 3C, respectively, are especially preferred. The structural formula of Flexzone 7 is:

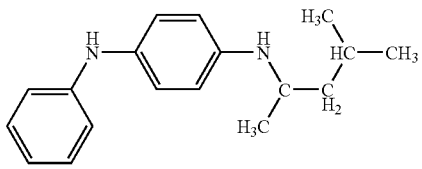

The structure of Flexzone 3C is:

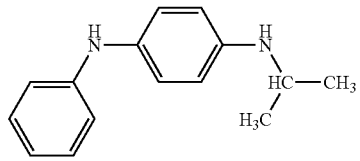

In the process of the present invention the N-alkyl-N'-phenyl-phenylenediamine is reacted with at least one olefin.

The olefins useful in the process of the present invention are not critical and include olefins which are both mono- or poly-unsaturated, cyclic or acyclic, substituted or un-substituted, and both terminal and internal olefins.

Examples of acyclic monoolefins include, but are not limited to, ethylene; propylene; butene-1; butene-2; isobutene; pentene-1; isopentene; pentene-2; hexene-1; hexene-2; 2-methyl pentene-1; 2-methyl pentene-2; n-decene-1; 2-ethyl octene-1; 2-ethyl octene-2; n-decene-2; dodecene-1; 2-ethyl decene-1; 2-ethyl decene-2; dodecene-2; octadecene-1; octadecene-2; 2-methyl heptadecene-1; di-isobutylene; eicosene-1; eicosene-2; 2-ethyl octadecene-1; docosene-1; docosene-2; triacontene-1; 2-ethyl octacosene-1; tetracontene-2; pentacontene-1; and the like.

Examples of cyclic monoolefins include, but are not limited to, cyclopentene, cyclohexene, cyclooctene, 1-methylcyclohexene, 1-butylcyclohexene, 1-methylcyclooctene, and the like.

Useful acyclic polyenes include, but are not limited to, 1,3-butadiene, 2-methyl-1,3-butadiene, 2,3-dimethyl-1,3-butadiene, 1,4-pentadiene, and the like.

Useful cyclic polyenes include, but are not limited to, cyclopentadiene, dicyclopentadiene, 1,3-cyclooctadiene, 1,3-cyclopentadiene, 1,4-octadiene, 1,3,5-cyclooctatriene, and the like.

Non-hydrocarbon olefins can be used, although these olefins are not preferred. They can have any substituents that do not interfere with the reaction. Examples of such substituents include, but are not limited to, halogens, alkoxy groups, aryloxy groups, aryl radicals, and the like. Illustrative examples of such non-hydrocarbon olefins are 2-chloro-3-butadiene, vinyl chloride, allyl chloride, vinyl bromide, ethyl vinyl ether, phenyl vinyl ether, butyl vinyl ether, lauryl acrylate, methyl acrylate, and the like.

In general, the most preferred olefin reactants are the hydrocarbon acyclic monoolefins comprising from 2 to about 50 carbon atoms, cyclic olefins comprising from 5 to 10 carbon atoms, and aryl-substituted monoolefins comprising from 8 to 20 carbon atoms.

The amount of olefin added will vary depending upon whether mono- or di-alkylation is desired. In general, from about 0.5 mole equivalent to 8 mole equivalents of olefin are added for each mole of N-alkyl-N'-phenyl-phenylenediamine. A most useful range is from about one mole equivalent to about three mole equivalents of olefin for each mole equivalent of N-alkyl-N'-phenyl-phenylenediamine.

The process proceeds best at elevated temperatures. A useful range is from about 50° to about 350° C. A preferred temperature range is from about 100° C. to about 300° C., more preferably from about 140° C. to about 240° C.

The pressure under which the reaction is conducted is not an independent variable, and varies with the temperature and vapor pressure of the reactants. With the more volatile lower olefins, such as ethylene, the reaction pressure will be quite high, while with the higher olefins only moderate pressures will be observed. Depending upon the reactants and the temperature, the pressure will normally range from about 10 to about 1800 psig, depending upon the olefin used.

The alkyl aluminum halides employed as catalysts in the practice of the present invention include any aluminum compound containing both an alkyl radical in which a carbon atom of the alkyl is bonded directly to an aluminum atom and also containing a halogen atom bonded directly to the aluminum atom. These include the dialkyl aluminum halides, the alkyl aluminum dihalides, and the alkyl aluminum sesquihalides. Some examples of suitable dialkyl aluminum halides are dimethyl aluminum bromide, diethyl aluminum bromide, diethyl aluminum chloride, di-n-propyl aluminum chloride, diisobutyl aluminum iodide, diisoamyl aluminum chloride, di-n-dodecyl aluminum chloride, and dieicosyl aluminum bromide. Examples of useful alkyl aluminum dihalides include methyl aluminum dichloride, ethyl aluminum dichloride, ethyl aluminum dibromide, n-propyl aluminum dichloride, isobutyl aluminum dibromide, n-hexyl aluminum dibromide, sec-decyl aluminum di-iodide, n-dodecyl aluminum dichloride, and n-eicosyl aluminum dibromide.

Both the above dialkyl aluminum halides and the alkyl aluminum dihalides are believed to exist in the form of dimers and these, of course, are included within the scope of the present invention.

Alkyl aluminum sesquihalides have the empirical formula $R_3Al_2X_3$, wherein R represents an alkyl group and X a halogen atom. Examples of useful alkyl aluminum sesquihalides include methyl aluminum sesquichloride, methyl aluminum sesquibromide, ethyl aluminum sesquichloride, ethyl aluminum sesquibromide, ethyl aluminum sesquiiodide, n-propyl aluminum sesquichloride, n-propyl aluminum sesquibromide, isobutyl aluminum sesquichloride, isobutyl aluminum sesquiiodide, n-hexyl aluminum sesquiiodide, n-decyl aluminum sesquichloride, n-dodecyl aluminum sesquibromide, and sec-eicosyl aluminum sesquichloride.

The above alkyl aluminum halides can be used individually or can be added to the aromatic amine as mixtures with good results.

The amount of alkyl aluminum halide added should be a catalytic amount. This means it should be sufficient to cause the olefin to alkylate the N-alkyl-N'-phenyl-phenylenediamine at a satisfactory rate under the reaction conditions employed. At higher temperatures and/or higher olefin concentrations, less catalyst is required. In general, good results are obtained if sufficient alkyl aluminum halide is added to the aromatic amine to provide one gram atom of aluminum for each 5-40 gram moles of N-alkyl-N'-phenyl-phenylenediamine, although more or less can be used. A more preferred operating range is the amount sufficient to provide one gram atom of aluminum for each 7-25 gram moles of N-alkyl-N'-phenyl-phenylenediamine, and a most preferred amount is that which provides one gram atom of aluminum per each 10-20 gram moles of N-alkyl-N'-phenyl-phenylenediamine.

The reaction time will vary to some extent with the reactants used. A greater influence is exerted by the reaction temperature and the amount of alkyl aluminum halide added. The process should be conducted until the desired degree of alkylation is attained. The progress of the reaction can be monitored by periodically withdrawing samples and analyzing them by vapor phase chromatography.

Various features and aspects of the present invention are illustrated further in the examples that follow. While these examples are presented to show one skilled in the art how to operate within the scope of the invention, they are not intended in any way to serve as a limitation upon the scope of the invention.

EXAMPLES

The following equation is provided to illustrate the features of the process of the present invention where decene is used as the olefin and diethyl aluminum chloride is used as the catalyst.

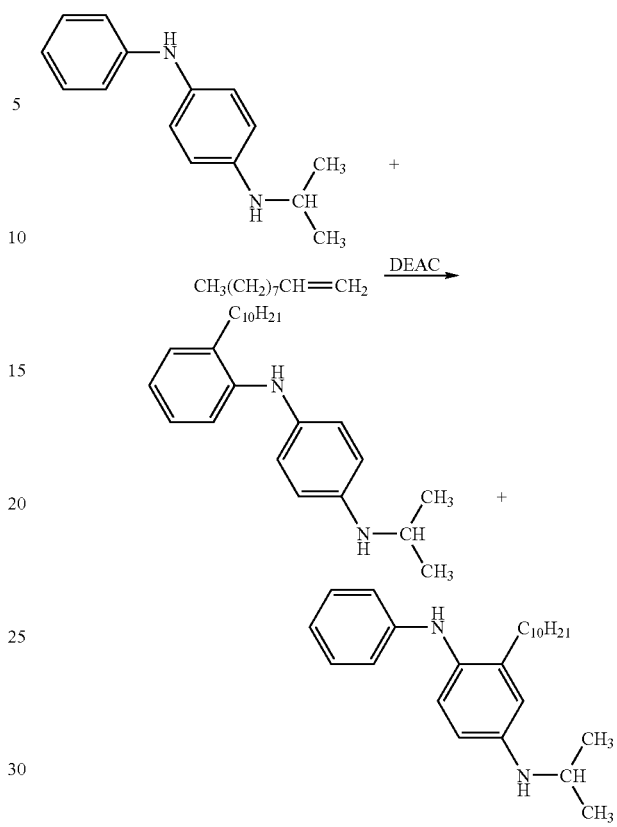

Depending upon the physical properties (gas or liquid) of the olefins used, there are two different procedures that can be used.

1. Light olefins (e.g., ethylene, propylene, butenes)

For a one liter autoclave, about 0.85 mole of N-alkyl-N'-phenyl-phenylene diamine is first loaded into the autoclave. The autoclave is sealed and pressure tested with 300 psig of nitrogen before releasing the vessel to atmospheric pressure. About 0.02-0.2 mole of diethyl aluminum chloride (DEAC) solution in hexane (catalyst) is injected with a syringe through a ball valve to the autoclave while protected by nitrogen. Then, a certain amount of light olefin, e.g, ethylene or propylene, is fed through an electric bottle. The vessel is then heated to a desired temperature with agitation, and kept at this temperature for a period of time (e.g., 2-24 hrs.). Finally, the reaction is stopped by cooling the autoclave down and releasing pressure from the vessel. A sample is then taken for analysis. Samples are also taken through a dip tube during the run to measure its progress. Examples of light olefins are shown in Table 1.

TABLE 1

Results of Direct Flexzone-7 Alkylation[a]

| Example | Catalyst | Olefin | Olefin/ Flexzone | Time (Hours) | Percent Flexzone Converion | Percent Yield[b] | | |
|---|---|---|---|---|---|---|---|---|
| | | | | | | Di-alkyl | Tri-alkyl A | Tri-alkyl B |
| 1 | DEAC | $C_2H_4$ | 3.8 | 16 | 88 | 47.2 | 33.2 | 4.9 |
| 2 | DEAC | $C_2H_4$ | 4.0 | 12 | 97 | 63.2 | 29.1 | 2.5 |
| 3 | DEAC | $C_3H_6$ | 6.4 | 16 | 93 | 81[c] | — | — |

[a]Reactions with DEAC as catalyst were run in a one liter hastelloy autoclave. Reactions were run at 180° C. for 15 hrs. Vessel contained 223 grams of Flexzone-7, 80 mL of 1 M DEAC in hexane (about 56 grams), and corresponding olefin.

TABLE 1-continued

Results of Direct Flexzone-7 Alkylation[a]

| Example | Catalyst | Olefin | Olefin/Flexzone | Time (Hours) | Percent Flexzone Converion | Percent Yield[b] | | |
|---|---|---|---|---|---|---|---|---|
| | | | | | | Di-alkyl | Tri-alkyl A | Tri-alkyl B |

[b]Yield of different products. Di-alkyl and tri-alkyl mean "dialkylation" and "tri-alkylation." Di-alkylation has one alkyl group on each of the two aromatic rings. Tri-alkyl A is three alkyl groups attached to Flexzone with two alkyl groups on the aromatic ring with one amino group and one alkyl group on the aromatic ring between amino groups.
[c]Mono propyl alkylated Flexzone about 7%

Olefins Used in Liquid Form.

In a one liter hastelloy autoclave, certain amounts of N-alkyl-N'-phenyl-phenylene diamine and olefin are loaded before the autoclave is sealed and pressure tested. A catalyst, such as DEAC in hexane or diisobutyl aluminum chloride (DIBAC), is injected through a syringe to the autoclave with nitrogen protection. Then, the reactor is heated to a desired temperature with agitation, and kept at this temperature for a period of time (e.g., 2-24 hrs). The reaction is stopped by cooling the reactor down to room temperature. Samples can be taken after or during the run to measure its yield or conversion. Examples of different liquid olefins are listed in Tables 2 through 5.

TABLE 2

Results of Direct Flexzone 3C Alkylation to Make GBFE[a]

| | Conditions | | | | % Sel. Mono[b] | | % Sel. |
|---|---|---|---|---|---|---|---|
| Example | Temp. (° C.) | Time (Hours) | DEAC:3C:Decene (Mole ratio) | % Conv. | Total | GBFE[c] | Di[b] |
| 4 | 180 | 15 | 1:10:15 | 59 | 88 | 57 | 11 |
| 5 | 220 | 15 | 1:10:10 | 63 | 89 | 52 | 11 |
| 6 | 200 | 15 | 1:5:5 | 75 | 81 | 45 | 18 |

[a]All reactions were run in a one liter hastelloy vessel. Total volume is about the same for all reactions (around 350 ml). Flexzone 3C and decene are loaded first. DEAC is put in through a syringe after the vessel is sealed, pressure tested, and $N_2$ purged.
[b]% Sel. Mono and % Sel. Di mean % selectivities to mono alkylation and di alkylation products respectively.
[c]The structure of GBFE is:

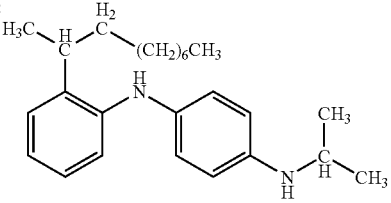

TABLE 3

Further Results of Direct Flexzone 3C Alkylation to Make GBFE[a]

| | Conditions | | | % Sel. Mono | | |
|---|---|---|---|---|---|---|
| Example | Temp. (° C.) | DEAC:3C:Decene (Mole ratio) | % Conv. | Total | GBFE | % Sel. Di |
| 7 | 180 | 1:5:7.5 | 92 | 71 | 46 | 29 |
| 8 | 160 | 1:5:7.5 | 79 | 87 | 66 | 13 |
| 9 | 180 | 1:10:15 | 70.5 | 89.2 | 58.1 | 11.8 |
| 10 | 180 | 1:10:10 | 68.2 | 90.5 | 60.5 | 9.5 |
| 11 | 160 | 1:5:5 | 77.3 | 87.5 | 67.2 | 12.5 |
| 12 | 180 | 1:5:5 | 89.4 | 76.3 | 52.2 | 2.7 |

[a]All reactions were run in a one liter hastelloy vessel. Total volume is approximately the same for all reactions (350 mL). Flexzone 3C and decene are loaded first. DEAC is put in through a syringe after the vessel is sealed, pressure tested, and $N_2$ purged. Reactions were run for 15 hours at temperature.

Example 13

Example 10 was repeated except that DIBAC was substituted for the DEAC employed therein. The percent conversion was 58; the percents Sel. Mono were 92.4 (total) and 63.5 (GBFE); and the percent Sel. Di was 7.6.

TABLE 4

Results of Direct GGFE Alkylation[a,b]

Conditions

| Examples | Temp. (° C.) | DEAC:GGFE:Decene (Mole ratio) | Time (hrs.) | % Conv. | % Sel. Mono |
|---|---|---|---|---|---|
| 14 | 180 | 1:10:10 | 5 | 22 | 79 |
| 15 | 220 | 1:5:5 | 4 | 73 | 74 |
| 16 | 195 | 1:5:5 | 4 | 61 | 92 |

[a]All reactions were run in a one liter vessel. Total volume is about the same for all reactions (around 300 mL). GGFE and decene are loaded first. DEAC is put in through a syringe after the vessel is sealed, pressure tested, and $N_2$ purged.
[b]GGFE is N-1,3-dimethyl butyl aniline.

TABLE 5

Flexzone 7 Ring Alkylation with Dicyclopentadiene[a]

| Example | Flexzone:olefin:DEAC (Mole ratio) | Temp. (° C.) | Time (hours) | % Conv. | S-a (%)[b] | S-b (%)[b] |
|---|---|---|---|---|---|---|
| 17 | 10:5:1 | 150 | 16 | 46.4 | 33.6 | 66.4 |
| 18 | 10:5:1 | 150 | 20 | 47.3 | 33.7 | 66.3 |
| 19 | 5:5:1 | 170 | 16 | 92.0 | 32.0 | 68.0 |
| 20 | 10:10:1 | 125 | 16 | 0 | — | — |
| 21 | 10:10:1 | 135 | 5 | 5.0 | 32.3 | 67.7 |
| 22 | 10:5:2 | 135 | 5 | 8.8 | 33.3 | 66.7 |

[a]Reaction was conducted in a one liter hastelloy autoclave. Flexzone 7 and dicyclopentadiene were loaded first. DEAC was injected with syringe with nitrogen protection after autoclave was sealed and pressure tested.
[b]S-a is the combination of selectivities to the two isomers with the alkylation on the ring between amino groups. S-b is the combination of selectivities to the isomers with alkylation on the aromatice ring connecting only the one amino. These two isomers have longer retention time on gas chromatography (GC).

The structure of dicyclopentadiene is:

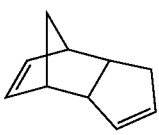

Dicyclopentadiene has four carbons that can attach to an aromatic ring. Two of the four alkylation isomers are alkylated on the aromatic ring between the amino groups and the other two are alkylated on the aromatic ring with only the one amino group.

In view of the many changes and modifications that can be made without departing from principles underlying the invention, reference should be made to the appended claims for an understanding of the scope of the protection to be afforded the invention.

What is claimed is:

1. A single-step process for the ring alkylation of at least one N-alkyl-N'-phenyl-phenylenediamine with at least one olefin selected from the group consisting of hydrocarbon acyclic monoolefins comprising from 2 to about 50 carbon atoms, cyclic olefins comprising from 5 to 10 carbon atoms, and aryl-substituted monoolefins comprising from 8 to 20 carbon atoms;

wherein said process comprises the single step of heating a mixture of the N-alkyl-N'-phenyl-phenylenediamine(s) and olefin(s) in the presence of a catalytic amount of at least one alkyl aluminum halide at a temperature of from about 50 to about 350° C. in a sealed vessel for from about one to about 30 hours.

2. The process of claim 1 wherein the the N-alkyl-N'-phenyl-phenylenediamine is of the structure:

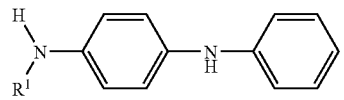

wherein $R^1$ is selected from the group consisting of alkyl, cycloalkyl, and radicals of the structural formula:

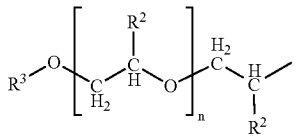

wherein $R^2$ may be the same or different and is independently selected from the group consisting of hydrogen and methyl, $R^3$ is selected from the group consisting of alkyl of from 1 to 12 carbon atoms and n is an integer of from 0 to 6.

3. The process of claim 2 wherein $R^1$ is selected from the group consisting of alkyls of from 1 to 50 carbon atoms and cycloalkyls of from 3 to 30 carbon atoms.

4. The process of claim 1 wherein the N-alkyl-N'-phenyl-phenylenediamine is selected from the group consisting of:
   N-methyl-N'-phenyl-p-phenylenediamine,
   N-ethyl-N'-phenyl-p-phenylenediamine,
   N-propyl-N'-phenyl-p-phenylenediamine,
   N-isopropyl-N'-phenyl-p-phenylenediamine,
   N-n-butyl-N'-phenyl-p-phenylenediamine,
   N-sec-butyl-N'-phenyl-p-phenylenediamine,
   N-n-pentyl-N'-phenyl-p-phenylenediamine,
   N-1-methylbutyl-N'-phenyl-p-phenylenediamine,
   N-(1-methylheptyl)-N'-phenyl-p-phenylenediamine,
   N-1,2-dimethylpropyl-N'-phenyl-p-phenylenediamine,
   N-2-methylbutyl-N'-phenyl-p-phenylenediamine,
   N-3-methylbutyl-N'-phenyl-p-phenylenediamine,
   N-1-ethylpropyl-N'-phenyl-p-phenylenediamine,
   N-n-hexyl-N'-phenyl-p-phenylenediamine,
   N-1-methylpentyl-N'-phenyl-p-phenylenediamine,
   N-2-methylpentyl-N'-phenyl-p-phenylenediamine,
   N-3-methylpentyl-N'-phenyl-p-phenylenediamine,
   N-4-methylpentyl-N'-phenyl-p-phenylenediamine,
   N-1,2-dimethylbutyl-N'-phenyl-p-phenylenediamine,
   N-1,3-dimethylbutyl-N'-phenyl-p-phenylenediamine,
   N-1-ethylbutyl-N'-phenyl-p-phenylenediamine,
   N-2-ethylbutyl-N'-phenyl-p-phenylenediamine,
   N-heptyl-N'-phenyl-p-phenylenediamine,
   N-octyl-N'-phenyl-p-phenylenediamine,
   N-nonyl-N'-phenyl-p-phenylenediamine,
   N-decyl-N'-phenyl-p-phenylenediamine,
   N-cyclooctyl-N'-phenyl-p-phenylenediamine,
   N-cyclohexyl-N'-phenyl-p-phenylenediamine,
   N-methylcyclohexyl-N'-phenyl-p-phenylenediamine, and
   N-cyclooctyl-N'-phenyl-p-phenylenediamine.

5. The process of claim 1 wherein the N-alkyl-N'-phenyl-phenylenediamine is selected from the group consisting of:
   N-(1,3-dimethylbutyl)-N'-phenyl-p-phenylenediamine,
   N-isopropyl-N'-phenyl-p-phenylenediamine,
   N-(1-methylheptyl)-N'-phenyl-p-phenylenediamine, and
   N-cyclohexyl-N'-phenyl-p-phenylenediamine.

6. The process of claim 1 wherein the N-alkyl-N'-phenyl-phenylenediamine is selected from the group consisting of N-(1,3-dimethylbutyl)-N'-phenyl-p-phenylenediamine and N-1isopropyl-N'-phenyl-p-phenylenediamine.

7. The process of claim 1 wherein from about 0.5 mole equivalent to 8 mole equivalents of olefin are added for each mole of N-alkyl-N'-phenyl-phenylenediamine.

8. The process of claim 1 wherein the alkyl aluminum halide is selected from the group consisting of dimethyl aluminum bromide, diethyl aluminum bromide, diethyl aluminum chloride, di-n-propyl aluminum chloride, diisobutyl aluminum iodide, diisobutyl aluminum chloride, diisoamyl aluminum chloride, di-n-dodecyl aluminum chloride, dieicosyl aluminum bromide, methyl aluminum dichloride, ethyl aluminum dichloride, ethyl aluminum dibromide, n-propyl aluminum dichloride, isobutyl aluminum dibromide, n-hexyl aluminum dibromide, sec-decyl aluminum di-iodide, n-dodecyl aluminum dichloride, n-eicosyl aluminum dibromide, methyl aluminum sesquichloride, methyl aluminum sesquibromide, ethyl aluminum sesquichloride, ethyl aluminum sesquibromide, ethyl aluminum ses-quiiodide, n-propyl aluminum sesquichloride, n-propyl aluminum sesquibromide, isobutyl aluminum sesquichloride, isobutyl aluminum sesquiiodide, n-hexyl aluminum sesquiiodide, n-decyl aluminum sesquichloride, n-dodecyl aluminum sesquibromide, and sec-eicosyl aluminum sesquichloride.

9. The process of claim 8 wherein the alkyl aluminum halide is selected from the group consisting of diethyl aluminum chloride and diisobutyl aluminum chloride.

10. A single-step process for the ring alkylation of at least one N-alkyl-N'-phenyl-phenylenediamine selected from the group consisting of N-(1,3-dimethylbutyl)-N'-phenyl-p-phenylenediamine and N-1isopropyl-N'-phenyl-p-phenylenediamine with at least one olefin selected from the group consisting of hydrocarbon acyclic monoolefins comprising from 2 to about 50 carbon atoms, cyclic olefins comprising from 5 to 10 carbon atoms, and aryl-substituted monoolefins comprising from 8 to 20 carbon atoms, wherein from about 0.5 mole equivalent to 8 mole equivalents of olefin are added for each mole of N-alkyl-N'-phenyl-phenylenediamine comprising wherein the single step of the process comprises heating a mixture of the N-alkyl-N'-phenyl-phenylenediamine(s) and olefin(s) in the presence of a catalytic amount of at least one alkyl aluminum halide selected from the group consisting of diethyl aluminum chloride and diisobutyl aluminum chloride at a temperature of from about 140 to about 240° C. in a sealed vessel for from about one to about 30 hours.

11. The process of claim 2 wherein from about 0.5 mole equivalent to 8 mole equivalents of olefin are added for each mole of N-alkyl-N'-phenyl-phenylenediamine.

12. The process of claim 2 wherein the alkyl aluminum halide is selected from the group consisting of dimethyl aluminum bromide, diethyl aluminum bromide, diethyl aluminum chloride, di-n-propyl aluminum chloride, diisobutyl aluminum iodide, diisobutyl aluminum chloride, diisoamyl aluminum chloride, di-n-dodecyl aluminum chloride, dieicosyl aluminum bromide, methyl aluminum dichloride, ethyl aluminum dichloride, ethyl aluminum dibromide, n-propyl aluminum dichloride, isobutyl aluminum dibromide, n-hexyl aluminum dibromide, sec-decyl aluminum di-iodide, n-dodecyl aluminum dichloride, n-eicosyl aluminum dibromide, methyl aluminum sesquichloride, methyl aluminum sesquibromide, ethyl aluminum sesquichloride, ethyl aluminum sesquibromide, ethyl aluminum ses-quiiodide, n-propyl aluminum sesquichloride, n-propyl aluminum sesquibromide, isobutyl aluminum sesquichloride, isobutyl aluminum sesquiiodide, n-hexyl aluminum sesquiiodide, n-decyl aluminum sesquichloride, n-dodecyl aluminum sesquibromide, and sec-eicosyl aluminum sesquichloride.

13. The process of claim 12 wherein the alkyl aluminum halide is selected from the group consisting of diethyl aluminum chloride and diisobutyl aluminum chloride.

* * * * *